US009027356B2

(12) United States Patent
Burke et al.

(10) Patent No.: US 9,027,356 B2
(45) Date of Patent: May 12, 2015

(54) BIOMATERIAL FREEZING

(71) Applicant: EMD Millipore Corporation, Billerica, MA (US)

(72) Inventors: Aaron Burke, Hamilton, MA (US); Michael Felo, Merrimack, NH (US); Brian Pereira, Derry, NH (US); Elias Noukas, Burlington, MA (US); Dennis Wong, Dedham, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/654,593

(22) Filed: Oct. 18, 2012

(65) Prior Publication Data

US 2013/0038469 A1 Feb. 14, 2013

Related U.S. Application Data

(62) Division of application No. 12/685,952, filed on Jan. 12, 2010.

(60) Provisional application No. 61/144,177, filed on Jan. 13, 2009.

(51) Int. Cl.
*F25D 25/00* (2006.01)
*F25D 21/00* (2006.01)
(Continued)

(52) U.S. Cl.
CPC .............. *F25D 29/00* (2013.01); *A01N 1/0263* (2013.01); *F25D 2600/06* (2013.01); *F25D 2700/12* (2013.01)

(58) Field of Classification Search
USPC .............................................. 62/62, 60, 371
See application file for complete search history.

(56) References Cited

U.S. PATENT DOCUMENTS 4,541,733 A 9/1985 Andre
4,582,100 A 4/1986 Poulsen
(Continued)

FOREIGN PATENT DOCUMENTS

CN 1823493 A 8/2006
EP 0356377 A1 2/1990
(Continued)

OTHER PUBLICATIONS

BioProcess International, Oct. 2004, Supplement, pp. 40-43, "Disposable Technology for Controlled Freeze-Thaw of Biopharmaceuticals at Manufacturing Scale", Voute, et al.
(Continued)

*Primary Examiner* — Cassey D Bauer
*Assistant Examiner* — Joseph Trpisovsky
(74) *Attorney, Agent, or Firm* — Nields, Lemack & Frame, LLC

(57) ABSTRACT

The biocontainer of the present invention provides a low cost, simple solution of many of the problems encountered during shipping, freezing and thawing of biopharmaceutical materials. The present invention enables a user to monitor the temperature profile of each biopharmaceutical container during the cryogenic process, so as to ensure the integrity of materials within each biocontainer by using a pre-installed and pre-sterilized temperature sensor. In some embodiments, the sensor assembly includes a wireless transmitter and is capable of transmitting information regarding the measured reading. In other embodiments, the sensor assembly includes a processing unit, which determines whether the temperature profile is acceptable. In a further embodiment, an indicator is included, such that the processing unit may indicate whether the biopharmaceutical material has been properly frozen. In other embodiments, the sensor assembly also includes a storage element, which is capable of storing various parameters during the freezing process.

12 Claims, 7 Drawing Sheets

(51) Int. Cl.
*F25D 3/08* (2006.01)
*F25B 49/00* (2006.01)
*F25D 29/00* (2006.01)
*A01N 1/02* (2006.01)

(56) References Cited

U.S. PATENT DOCUMENTS

| | | | |
|---|---|---|---|
| 4,788,871 | A | 12/1988 | Nelson et al. |
| 5,355,684 | A | 10/1994 | Guice |
| 5,939,023 | A | 8/1999 | Coelho et al. |
| 6,635,414 | B2 | 10/2003 | Wisniewski |
| 6,726,671 | B2 | 4/2004 | Dumont et al. |
| 7,372,003 | B2 * | 5/2008 | Kates .................. 219/494 |
| 7,405,667 | B2 | 7/2008 | Abe et al. |
| 7,412,846 | B2 | 8/2008 | Sekiya et al. |
| 8,177,123 | B2 | 5/2012 | Voute et al. |
| 2003/0037554 | A1 | 2/2003 | Gatling et al. |
| 2003/0066295 | A1 | 4/2003 | Wisniewski et al. |
| 2004/0066835 | A1 | 4/2004 | Drews |
| 2005/0016198 | A1 | 1/2005 | Wowk et al. |
| 2005/0077029 | A1 | 4/2005 | Morales Cervantes et al. |
| 2005/0136161 | A1 | 6/2005 | Okita |
| 2006/0208881 | A1 | 9/2006 | Suzuki |
| 2007/0000910 | A1 * | 1/2007 | Faries et al. ............ 219/506 |
| 2007/0267419 | A1 | 11/2007 | Fuhr et al. |
| 2007/0277436 | A1 | 12/2007 | Jones et al. |
| 2008/0120984 | A1 | 5/2008 | Shaham et al. |
| 2008/0199370 | A1 | 8/2008 | Mourtada et al. |
| 2010/0175393 | A1 | 7/2010 | Burke et al. |
| 2013/0039382 | A1 | 2/2013 | Burke et al. |

FOREIGN PATENT DOCUMENTS

| | | |
|---|---|---|
| JP | 2004-3569 A | 1/2004 |
| JP | 2004-527720 A | 9/2004 |
| JP | 2006-240809 A | 9/2006 |
| WO | 02/095306 A1 | 11/2002 |

OTHER PUBLICATIONS

International Search Report/Written Opinion mailed Mar. 22, 2010 in corresponding PCT application No. PCT/US2010/020744.
International Preliminary Report on Patentablility mailed Jul. 28, 2011 in corresponding PCT application No. PCT/US2010/020744.
Office Action-Restriction- mailed Oct. 2, 2012 in corresponding U.S. Appl. No. 12/685,952.
Office Action mailed Nov. 1, 2012 in corresponding U.S. Appl. No. 12/685,952.
Final Rejection mailed Apr. 22, 2013 in corresponding U.S. Appl. No. 12/685,952.
Final Rejection mailed Mar. 19, 2013 in corresponding U.S. Appl. No. 12/685,952.
Japanese Communication, with English translation, mailed Dec. 18, 2012 in corresponding Japanese patent application No. JP 2011-546300.
Chinese Communication, with English translation, issued Dec. 5, 2012 in corresponding Chinese patent application No. CN 201080011722.7.
Japanese Communication, with English translation, mailed Oct. 1, 2013 in corresponding Japanese patent application No. JP 2011-546300.
Final Rejection mailed Feb. 10, 2014 in corresponding U.S. Appl. No. 12/685,952.
Final Rejection mailed Feb. 10, 2014 in corresponding U.S. Appl. No. 13/654,595.
Office Action mailed Aug. 28, 2013 in corresponding U.S. Appl. No. 12/685,952.
Office Action mailed Oct. 16, 2013 in corresponding U.S. Appl. No. 13/654,595.
Office Action mailed Jun. 16, 2014 in corresponding U.S. Appl. No. 12/685,952.
Office Action mailed Jun. 27, 2014 in corresponding U.S. Appl. No. 13/654,595.
Final Rejection mailed Nov. 14, 2014 in corresponding U.S. Appl. No. 13/654,595.
Notice of Allowance mailed Nov. 20, 2014 in corresponding U.S. Appl. No. 12/685,952.
Notice of Allowance mailed Feb. 5, 2015 in corresponding U.S. Appl. No. 13/654,595.

* cited by examiner

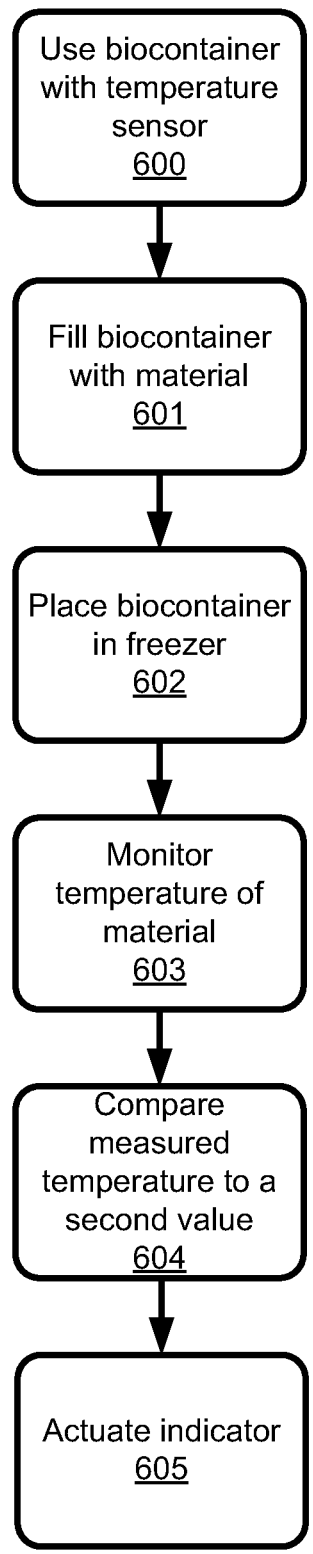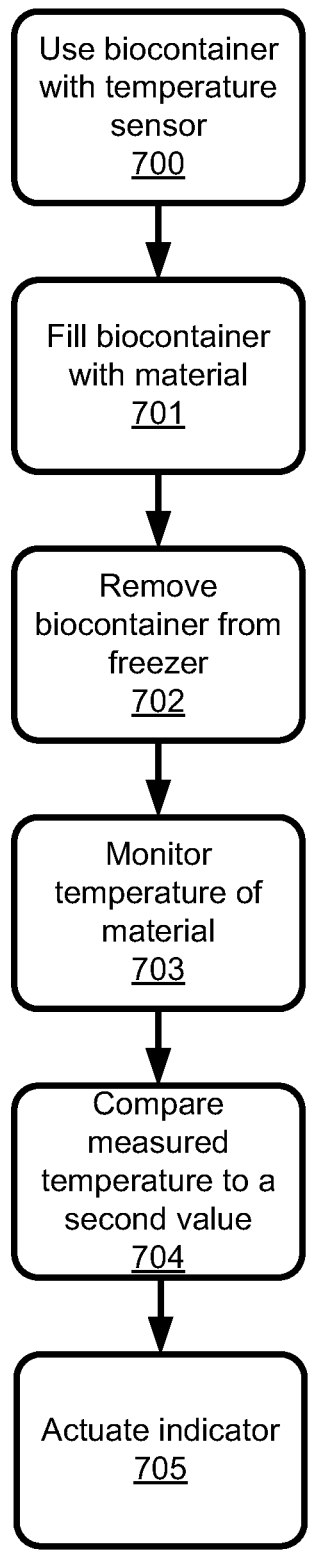
FIG. 6
FIG. 7

BIOMATERIAL FREEZING

This application is a divisional of U.S. patent application Ser. No. 12/685,952 filed Jan. 12, 2010, and claims priority of U.S. Provisional Patent Application Ser. No. 61/144,177, filed Jan. 13, 2009, the disclosure of which is incorporated herein by reference in its entirety.

BACKGROUND OF THE INVENTION

The preservation of biopharmaceutical materials is essential in the manufacture and storage of these productions. One traditional method used to preserve these pharmaceutical materials is through freezing, also known as cryopreservation.

Biopharmaceutical materials are often frozen and thawed throughout the manufacturing process, as well as afterwards, such as during shipping. Freezing these materials reduces the chances of degradation, microbial contamination and denaturing that can occur at room temperature. For example, cryopreservation allows materials to be partially prepared, and then stored in an intermediate condition, thus decoupling the various activities involved in the manufacture of the product. In order to do so, they are often placed in storage containers, often referred to as biocontainers, ranging in size from a few milliliters to thousands of liters. In some instances, the biocontainers are made from a plastic material with a fixed form. Other biocontainers are more flexible and can take on a multitude of forms. In certain instances, these biocontainers are placed within frames, carriers or other structures that define their shape.

However, in order for cryopreservation to be successful, careful attention must be paid to the operating parameters. It has been reported that the rate at which biopharmaceutical materials are frozen is critical to their continued utility. For example, if the material is frozen too slowly, the diffusion of solutes in liquid bulk is exacerbated, leading to potential issues such as a pH shift, increased ionic strength, and phase separation. In addition, problems such as the formation of small ice crystals within the biopharmaceutical material, e.g., within a protein structure, can stress the material causing, for example, denaturation of the protein. Denaturation is often indicated by unfolding of the protein, thereby causing it to lose its efficacy, and potentially aggregating.

Within a bulk sample, denaturation of material can occur non-uniformly due to non-uniformities in the heat cycles. For instance, a frozen sample exposed to an instantaneous heat source during transport can cause the outer surface to melt. Ideally, a uniform freeze rate across the sample would reduce local denaturation as molecules within the interface layer may experience excessive shear.

To attempt to mitigate several of these issues, custom freezers have been developed, e.g., where the freezer has one or more temperature sensors that are an integral part of the freezer. These integral temperature sensors are either placed inside the biocontainer or positioned such that they abut the biopharmaceutical container, thereby allowing them to record the temperature of the contents of the biocontainer. Based on the measured reading of such a sensor, the freezer adjusts its operating parameters, either attempting to cool more quickly or to maintain the temperature.

While such freezers may be useful in proper cryopreservation, there are many drawbacks. For example, the user is forced to buy a complete system in order to receive the benefits. In addition, the capacity of the freezer may be limited, or the number of temperature sensors may be limited. In other words, while one biocontainer may have a temperature sensor to monitor its temperature profile during the freezing process, other biocontainers within the same freezer may not be properly monitored. This can be problematic as the temperature profile varies within the freezer enclosure. For example, a biocontainer near the door may experience condensation thereby creating different heat conduction pathways. Biocontainers located near the interior walls may freeze more quickly. Furthermore, these freezers only monitor the temperature of the biopharmaceutical material while in the freezer. Any variations in temperature experienced during transit or during the thawing process are not monitored.

Therefore, there exists a need for a low cost, simple solution that enables the user to monitor the temperature profile of each biopharmaceutical container during the cryogenic process, so as to insure the integrity of each biocontainer. Furthermore, a method of monitoring the temperature during the thawing process and during transit would be advantageous.

SUMMARY OF THE INVENTION

The present invention provides a biopharmaceutical container (biocontainer) having an integrated temperature sensor.

The biocontainer of the present invention provides a low cost, simple solution for many of the problems encountered during shipping, freezing and thawing of biopharmaceutical materials. The present invention enables a user to monitor the temperature profile of each biopharmaceutical container during the cryogenic process, so as to ensure the integrity of materials within each biocontainer. In order to meet the requirements of the biopharmaceutical freezing process, the biopharmaceutical container includes a pre-installed and pre-sterilized temperature sensor. Also provided herein are methods of monitoring the temperature during the freezing and thawing process.

In some embodiments, the sensor assembly is positioned within the biocontainer so as to be at or near the thermal center of the material. In certain embodiments, a sensor attachment mechanism, which is attached to one or more points on the biocontainer, is used to hold the sensor assembly in place. Since it is necessary that the interior of the biocontainer be sterile before the introduction of the pharmaceutical material, the sensor components are constructed of materials that can be readily sterilized. In certain embodiments, the temperature sensor is constructed utilizing Silicon on Insulator (SOI) technology, so that it can withstand sterilization, such as gamma sterilization, after it has been inserted into the biocontainer.

The presence of an integrated temperature sensor in the biopharmaceutical container allows numerous functions to be performed. In some embodiments, the sensor assembly includes a wireless transmitter and is capable of transmitting information regarding the measured reading. In other embodiments, the sensor assembly includes a processing unit, which determines whether the temperature profile is acceptable. In a further embodiment, an indicator, such as a visual indicator, is included, such that the processing unit may indicate whether the biopharmaceutical material has been properly frozen. In other embodiments, the sensor assembly also includes a storage element, which is capable of storing various parameters during the freezing process.

BRIEF DESCRIPTION OF THE DRAWINGS

FIG. 6 shows a flowchart of a freezing process;

FIG. 7 shows a flowchart of a thawing process; and

DETAILED DESCRIPTION OF THE INVENTION

As described above, the need to monitor and insure the temperature profile of a biopharmaceutical material while it undergoes cryopreservation is imperative. Furthermore, it is important to be able to monitor the temperature of a biopharmaceutical material during other steps in the manufacturing and delivery process, such as transit.

Figure 1:
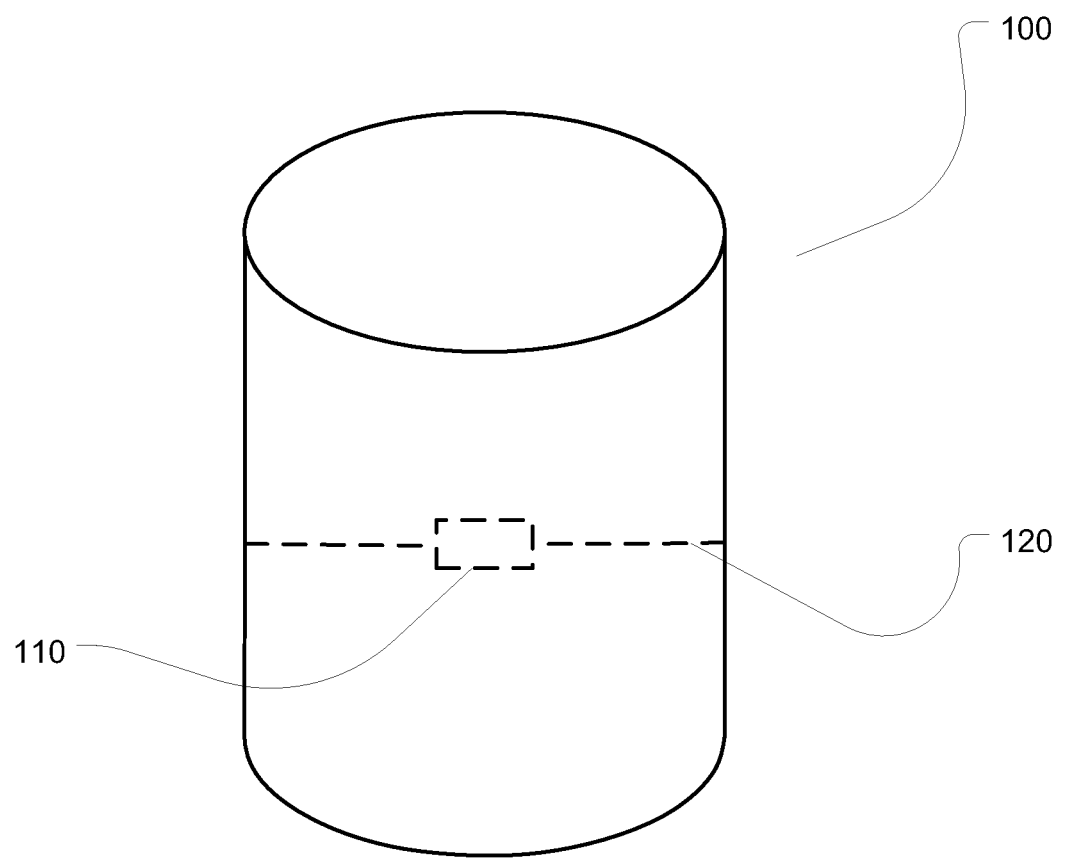
FIG. 1 shows a first embodiment of an apparatus of the present invention.

In various embodiments according to the present invention, the biopharmaceutical material can be, but is not limited to, an amino acid, a peptide, a protein, a DNA molecule, an RNA molecule, a drug, an enzyme, an antibody or fragment thereof, a tissue or fragment thereof, an organ or fragment thereof, a preservative, a blood product, a cell, a cellular organelle, an inclusion body, and a cellular aggregate. Furthermore, the material may be serum, blood, plasma, an amino acid formulation, a protein formulation, a nucleic acid formulation, and a cell culture media formulation FIG. 1 shows a first embodiment of an apparatus of the present invention. A biocontainer 100 is used to hold a biopharmaceutical material. This biocontainer is typically constructed of a suitable plastic, such as polyethylene or a laminate material like the Millipore PureFlex™ film. This material is preferable as it is flexible, low cost and able to withstand sterilization, such as gamma irradiation. A sensor assembly 110 is affixed within the biocontainer 100, such as via a sensor attachment mechanism 120. In some embodiments, this attachment mechanism 120 is a sleeve that can be sealed, so as to protect the sensor assembly from the biopharmaceutical material. In certain embodiments, the plastic sleeve is sealed after the sensor is installed. In other embodiments, the attachment mechanism is a flexible material with an overcoating or sealable enclosure located at a predetermined location. The sensor assembly is located within this overcoating or sealable enclosure. The attachment mechanism 120 is preferably constructed of materials similar to those used for the biocontainer so as to retain the overall flexibility and usefulness.

The biocontainer 100, attachment mechanism 120 and sensor assembly 110 may then all be sterilized simultaneously. This sterilization can be of any suitable means, including but not limited to autoclaving, gas sterilization, such as using ETO (ethylene oxide) gas, and gamma sterilization. To allow the sensor assembly to be positioned within the attachment mechanism during sterilization, it is preferable that it be manufactured using a process with a high resistance to gamma radiation, such as Silicon on Insulator (SOI). In other embodiments, traditional semiconductor manufacturing processes are used to produce the sensor assembly, and the assembly is sterilized using autoclaving. Once the biocontainer has been sterilized, it is ready for use.

Regardless of the mechanism used to hold and protect the sensor assembly, the temperature sensor is preferably positioned within the biocontainer such that, when the biocontainer is full or nearly full, the temperature sensor is roughly at the thermal center of the material. This is preferably achieved by locating the temperature sensor at or near the geometric center of a filled biocontainer. The geometric center is determined based on the shape of the filled biocontainer. For example, the geometric center of a rectangular prism is found by connecting opposite diagonals. The intersection of these diagonals is the geometric center. In the case of a cylinder, the geometric center is the center of the circle, located at a position equal to one half of the height. Similarly, those of ordinary skill in the art are able to determine the center of other volumetric shapes.

By being located at the geometric center of the filled biocontainer, the temperature sensor is able to take temperature measurements of the last point within the biocontainer to freeze, as the geometric center of a filled biocontainer is the same location as the thermal center of the material, assuming the density and composition of the biopharmaceutical material is uniform throughout the biocontainer. Of course, if the biocontainer is less than completely filled to its volumetric capacity, the geometric center of the biocontainer may not correspond to the thermal center of the material.

Without wishing to be bound by theory, it is contemplated that even in instances where the biocontainer is not intended to be filled to its full volumetric capacity, one of ordinary skill in the art may incorporate a temperature sensor at or near the thermal center of a predetermined volume of liquid placed inside the biocontainer. For example, a biocontainer may be intended to be filled to less than full volumetric capacity, however, to a predetermined volume. Accordingly, the position at which the temperature sensor is placed inside the biocontainer may be calculated based on the thermal center of a predetermined volumetric capacity of the liquid contained inside the biocontainer, where the thermal center does not necessarily correspond to the geometric center of the biocontainer, but to the thermal center of the predetermined volume of liquid. Accordingly, such a biocontainer can be subsequently provided for use with the specific predetermined volume of liquid. In a further embodiment, a biocontainer including a temperature sensor is provided with instructions for use with a predetermined volume of liquid, where the temperature sensor is positioned at or near the thermal center of the predetermined volume of liquid.

Since placing the sensor at exactly the geometric center of a filled container may be difficult, the present invention also includes placing the sensor near the geometric center. It is obvious to one skilled in the art, that placement close to, but not at, the geometric center will achieve all of the benefits described herein. Thus, the expression "at the geometric center" also includes those locations within proximity such that their thermal behavior is similar to that of the actual geometric center.

Figure 2:
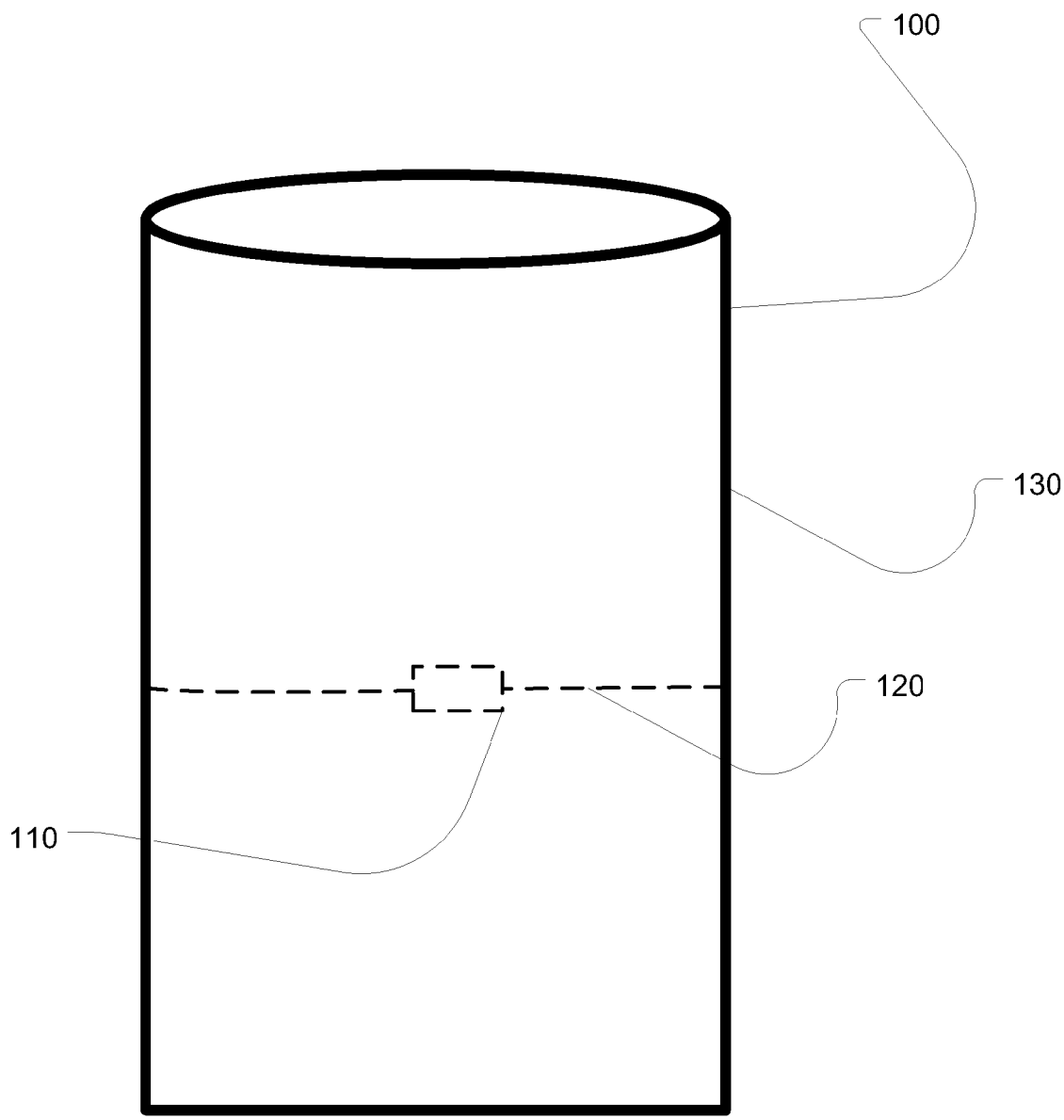
FIG. 2 shows the outer surface of the biocontainer of the present invention.

Returning to FIG. 1, the sensor attachment mechanism 120 is shown as extending across the center of a biocontainer. In certain embodiments, exemplified in FIG. 2, a seam 130 exists along the outer edges of the biocontainer. When the various pieces of plastic are being assembled and fused together, the attachment mechanism 120 is inserted into the seam 130 on opposite sides of the biocontainer 100. In this way, the attachment mechanism 120 is fused directly to the biocontainer 100 during the biocontainer manufacturing process, thereby minimizing manufacturing steps and handling.

Figure 3:
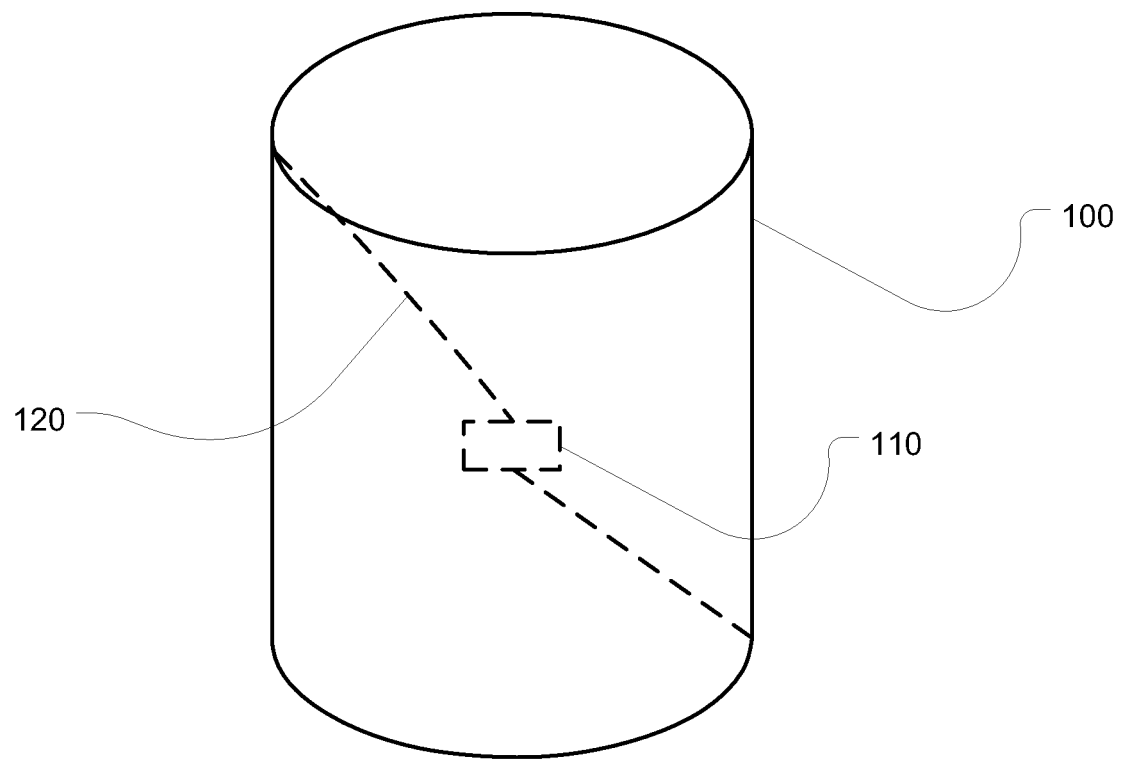
FIG. 3 shows a second embodiment of an apparatus of the present invention.

While FIG. 1 shows the attachment mechanism 120 extending horizontally across the biocontainer, the attachment mechanism 120 can be installed in any orientation, as long as it passes through the geometric center of the filled biocontainer. FIG. 3 shows an alternate embodiment, wherein the sensor 110 is held in place via an attachment mechanism 120 that is connected at the upper left corner and lower right corner. Other attachment points are also envisioned and within the scope of the invention.

In another embodiment, a larger piece of plastic is used. This piece is then folded over onto itself, and fused along the open edges. In this embodiment, the attachment points, such as those shown in FIG. 3, must be located where the open edges are fused together.

As seen in the above Figures, the sensor attachment mechanism 120 includes a physical extension from the sidewalls of the biocontainer to the enclosed electronics. This extension may include a thin film or a plastic strand or string to retain the electronics within the thermal center. In some embodiments, a thermoplastic material of similar construction to that of the biocontainer is used. The shape and size of the extension preferably has a minimal effect on the overall thermal signature of the biocontainer. This is particularly important so as to reduce thermal abnormalities due to conduction along the extension.

Figure 5:
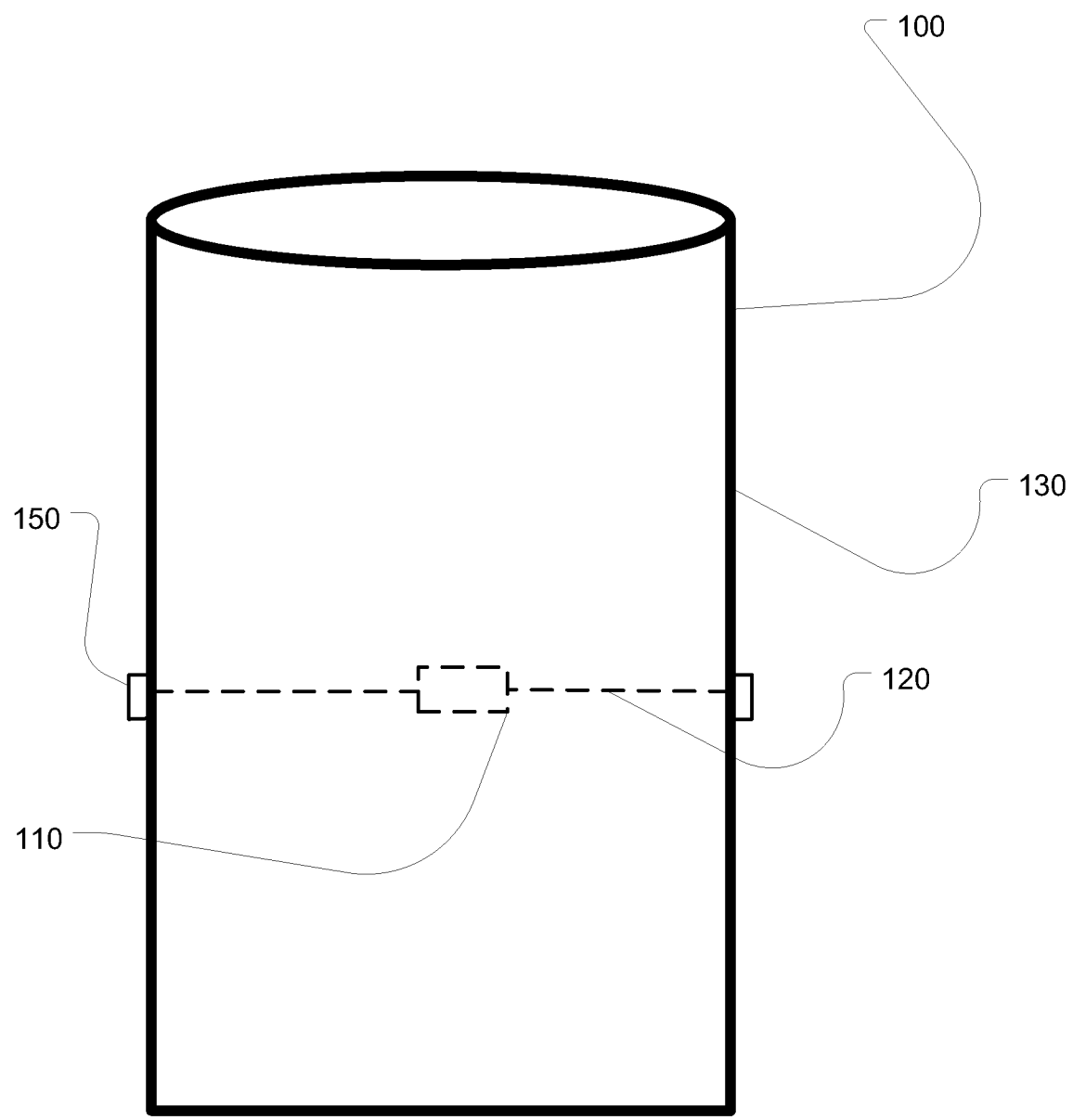
FIG. 5 shows another embodiment of the present invention.

FIG. 5 shows another embodiment used to position the sensor assembly 120 in the proper location. In this embodiment, the biocontainer 100 includes ports 150 which are typically attached to the biocontainer 100 using a fusing or welding process. In other words, the ports are attached to the biocontainer 100 over preexisting openings in the biocontainer 100 so that biological material can enter or exit the container. The sensor attachment mechanism 120 can be attached to the biocontainer 100 using these ports 150. In one embodiment, the sensor attachment mechanism 120 is fused to the port and biocontainer while the port 150 is being affixed to the biocontainer 100. In another embodiment, the sensor attachment mechanism 120 is affixed via mechanical means to the port 150. For example, the sensor attachment mechanism 120 may have ends that can be mechanically affixed onto or over the ports 150. A loop at the end of the sensor attachment mechanism 120 can be used to loop over the external protruding port 150.

The sensor attachment mechanism 120 is used to position the sensor assembly in the proper location. As described above, in some embodiments, the attachment mechanism contains a protective overcoating or enclosure, such as a plastic enclosure, in which the sensor assembly is located and sealed. This provides a fluid tight barrier between the sensor assembly and the biopharmaceutical material. In other embodiments, a plastic sleeve is used in which the sensor is placed prior to being fused to the other plastic pieces of the biocontainer. Other common methods of isolating electronics from the environment include epoxy coatings or thermal plastic in-molding.

Within the enclosure is a sensor assembly, which includes a temperature sensor, capable of measuring the temperature of the surrounding biopharmaceutical material. To minimize the number of connections, and the potential for contamination and error, the sensor assembly preferably has no wires extending out of the biocontainer. Thus, the sensor assembly preferably operates wirelessly.

A temperature sensor can be employed in a number of ways. In one embodiment, the temperature sensor is unpowered, and simply relays the current temperature measurement when energized by a remote reader, such as a RFID reader. Thus, in one embodiment, the sensor assembly includes at least one temperature sensor, an attached antenna to receive and transmit RFID signals, and the power circuit needed to convert the electromagnetic power from the RFID reader to electrical power to operate the at least one temperature sensor. Also, a remote RFID reader must query the sensor at regular intervals to determine the temperature profile of the biopharmaceutical material during the cryopreservation process.

In another embodiment, a temperature sensor is powered. In certain embodiments, the sensor assembly is powered by a battery contained within the enclosure. The battery is housed such that it is unaffected during the sterilization process. In still other embodiments, the sensor assembly is powered wirelessly, such as via electromagnetic waves or magnetic induction fields. These electromagnetic fields are created by a remote powered antenna. In some embodiments, the remote powered antenna is located within the freezer to maximize energy transfer. In a further embodiment, an unpowered focusing coil is also used to enhance the field near the biocontainer(s). To capture the transmitted electromagnetic waves, the sensor assembly may also contain an antenna. This antenna receives electromagnetic waves, which it then converts to electrical power, which is used to operate the sensor and other electrical components.

In another embodiment, the sensor assembly includes a storage element, such as a memory device. In some embodiments, nonvolatile memory is used, due to its ability to retain data even in the absence of electrical power. The storage element is used to store temperature readings at various times, such as at regular intervals. Later, when the biocontainer is thawed, the operator can interrogate the embedded storage element via a wireless protocol to determine the temperature profile that the biopharmaceutical material underwent. By comparing the stored data to predetermined acceptable limits, the operator can determine whether the material was properly frozen and/or thawed and is therefore acceptable to use.

To perform this query, a variety of wireless protocols including, but not limited to Zigbee, Bluetooth, RFID, Wifi, and 802.11a/b/g/n, may be used.

Figure 4:
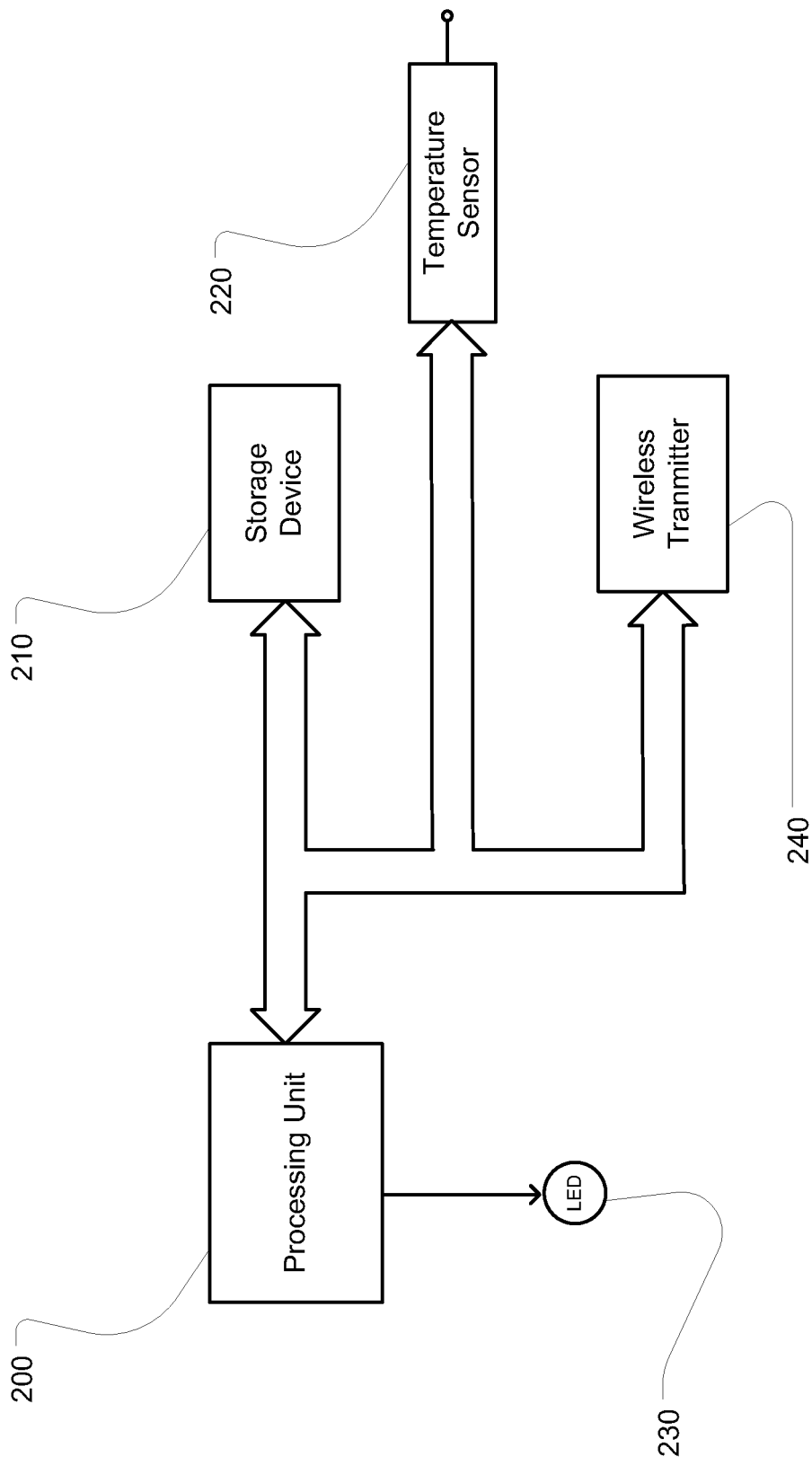
FIG. 4 shows the internal circuit components according to one embodiment of the present invention.

In another embodiment, shown in FIG. 4, a processor 200 and a storage element 210 are incorporated in the sensor assembly with the temperature sensor 220. In addition to storing data as described above, the storage element may contain instructions for the execution of the processor 200. The incorporation of a processor 200 allows the biocontainer to have increased functionality. In some embodiments, the sensor assembly also contains an indicator 230, such as a visual indicator, that is used to alert the user as to whether the material was properly frozen. In this embodiment, the processor 200 analyzes the sensor readings in comparison to acceptable limits and determines whether the material was properly frozen and is therefore useable. For example, the measured temperature values may be compared to a reference temperature profile. This reference temperature profile may include a range of acceptable temperatures as a function of time. In another embodiment, the processor 200 may compare the current measured temperature to one or more previous measured temperatures to determine whether the freezing process was properly completed. This determination is then conveyed via the indicator 230. In one example, a red LED is used to convey failure; in other embodiments, a green LED conveys success.

In another embodiment, this determination of the success of the freezing process is stored in the storage element 210. In this way, the operator simply queries the storage element 210 to determine the result. In yet another embodiment, a wireless signal is transmitted from a transmitter 240 on the sensor assembly, conveying the status of the freezing process. While the above description discloses several ways in which the results of the freezing process can be conveyed, this list is not intended to be inclusive. Other methods of conveying the results are contemplated and within the scope of the invention.

FIG. 6 shows a flowchart of the steps used to monitor the freezing process of a material. First, as shown in Box 600, a sterilized biocontainer having a predetermined volumetric capacity is provided. This biocontainer includes a wireless temperature sensor positioned at or about the geometric center of the biocontainer. The biocontainer is then filled with biopharmaceutical material, as shown in Box 601. The biocontainer is then placed in the freezer as shown in Box 602.

The temperature sensor is then used to monitor the temperature within the biocontainer as the material freezes, as shown in Box 603. In some embodiments, the measured temperature values are stored in a storage element, which is in communication with the temperature sensor. In other embodiments, the measured temperature values are transmitted wirelessly by a transmitter in communication with the wireless transmitter.

In other embodiments, a processing unit is in communication with the temperature sensor and performs additional functions. For example, the processor may compare the measured temperature value to a second temperature, as shown in Box 604. This second temperature may be a previously measured temperature value. In other embodiments, this second temperature is obtained from a reference temperature profile, which is stored in the storage element.

In the event that the comparison indicates that the freezing process is defective, an indicator is actuated, as shown in Box 605. This indicator may be an alarm, such as an audio or visual alarm. In other embodiments, the indicator may be a data pattern written to the storage element. In other embodiments, the measured temperatures may all be stored in the storage element. These can then be read by the operator at a later time.

This functionality also allows the present invention to serve as a validation tool. In another words, once the biocontainer has been successfully frozen (as determined using one or more of the techniques described above), the operator can be confident that the freezing profile used would be applicable to freeze other biocontainers containing the same material. Thus, one or more such biocontainers can be used to validate a new or modified freezing profile quickly.

In addition to being used to monitor and verify the freezing process, the sensor assembly can also be used to control it. The ability to measure temperature and wirelessly communicate allows the sensor assembly to feedback information to the freezer. In some embodiments, the sensor assembly simply transmits the current temperature of the material. The freezer, using techniques known and described in the prior art, then adjusts its cooling process based on this information. If multiple biocontainers are placed within a single freezer, then the freezer can determine not just the temperature of each biocontainer, but also develop a map of the entire freezer enclosure.

While this sensor assembly is useful during the actual freezing process, it can serve other purposes as well. For example, the sensor assembly may also monitor the temperature profile of the material as it is thawed to ensure that the profile meets acceptable parameters. For example, the thawing process may include a reference temperature profile. This profile may include a range of acceptable temperatures as a function of time. As the material is thawed, the temperature is compared to this reference profile and a determination is made as to whether the thaw process is acceptable. In another embodiment, the thawing process is tracked by measuring the change in the temperature of the material between successive readings. If the deviation of the measured temperature from this second temperature (either the reference temperature or the previous measurement) is too great, an indicator is actuated. The indicator may be an audio or visual alarm, or in other embodiments, may be a data pattern stored in the storage element. In other embodiments, all of the measured temperatures are stored in the storage element. The integrity of the process is then checked at a later time by reviewing the values stored in the storage element. A flowchart of a representative thawing process is shown in FIG. 7.

Additionally, the sensor assembly can be used to verify the integrity of the material as it is moved in transit to other locations. For example, while in transit, the material may have to remain within predetermined temperature limits. The sensor assembly may continually monitor the temperature of the material to insure that it remains within this range. The actual measured temperature may be compared to a reference temperature or a reference range. The results of this comparison can then be indicated to the user. In one embodiment, the results of the comparison are stored in a storage element in communication with the temperature sensor. In another embodiment, an alarm, such as an audio or visual signal, may be actuated in response to the results of the comparison. In other embodiments, all of the measured temperatures are stored in the storage element. The integrity of the process is then checked at a later time by reviewing the values stored in the storage element.

Figure 8:
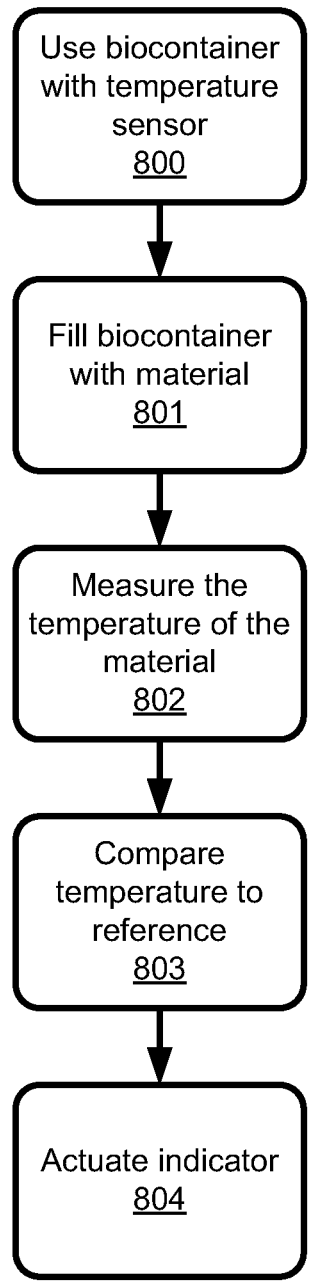
FIG. 8 shows a flowchart for monitoring the material temperature while in transit.

FIG. 8 shows a flowchart that illustrates the monitoring of biopharmaceutical material in transit. As before, a biocontainer having a temperature sensor located at or near its geometric center is used, as shown in Box 700. The bag is filled with material, as shown in Box 801. The temperature sensor than monitors the temperature of the material, as shown in Box 802. The measured temperature may be compared to a second temperature, as shown in Box 803. This second temperature may be a previous measured temperature (in case the rate of temperature change is of interest), or may be a reference temperature or range. If the deviation of the measured temperature from this second temperature is too great, an indicator is actuated, as shown in Box 804. The indicator may be an audio or visual alarm, or in other embodiments, may be a data pattern stored in the storage element.

In another embodiment, a plurality of temperature sensors is used. As described above, the first sensor is located in the geometric or thermal center of the biocontainer. Additional sensors may be located along the outer edges. These sensors are particularly useful in detecting biopharmaceutical material thaw. For example, a sensor located along the upper and lower end of the sensor attachment mechanism in FIG. 3 would allow monitoring of the biocontainer at two opposite locations where premature or unintended thawing may take place.

What is claimed is:

1. A method for monitoring the freezing of a biopharmaceutical material contained in a biocontainer, the method comprising the steps of:
providing a sterilized biocontainer of a predetermined volumetric capacity comprising an indicator to indicate whether said biopharmaceutical material was properly frozen, a storage element, and a sensor attachment mechanism affixed to opposite edges of said biocontainer, disposed within said biocontainer and passing through the geometric center of said biocontainer, said sensor attachment mechanism comprising a sealed enclosure holding a wireless temperature sensor, said wireless temperature sensor positioned at or about the geometric center of said biocontainer, wherein said storage element is in communication with said temperature sensor;
filling said biocontainer to its volumetric capacity with said biopharmaceutical material;

placing said biocontainer in a cryofreezer, thereby to freeze said biopharmaceutical material contained therein;

using said sensor to monitor the temperature of said biopharmaceutical material at said geometric center;

storing data from said sensor in said storage element;

allowing said biopharmaceutical material to freeze;

providing a processing unit in communication with said temperature sensor, said indicator, and said storage element;

comparing, by said processing unit, temperature data from said wireless temperature sensor to predetermined values to determine whether, once frozen, said biopharmaceutical material was properly frozen;

actuating said indicator by said processing unit to indicate the result of said determination of whether said biopharmaceutical material was properly frozen.

2. The method of claim 1, further comprising:

providing a wireless transmitter in communication with said temperature sensor; and transmitting data from said storage element via said wireless transmitter.

3. The method of claim 1, wherein comparing, by said processing unit, temperature data from said wireless temperature sensor to predetermined values comprises comparing data from said sensor to previous data from said sensor stored in said storage element.

4. The method of claim 1, wherein said biocontainer is held in place by a frame, carrier or other structure.

5. The method of claim 1, wherein comparing, by said processing unit, temperature data from said wireless temperature sensor to predetermined values comprises comparing data from said sensor to a reference temperature profile stored in said storage element.

6. The method of claim 1, wherein said indicator comprises a visual indicator.

7. The method of claim 6, wherein said indicator comprises an LED.

8. The method of claim 1, wherein said indicator comprises an audio alarm.

9. The method of claim 1, further comprising storing said determination of whether said biopharmaceutical material was properly frozen on said storage element.

10. The method of claim 1, further comprising transmitting said determination of whether said biopharmaceutical material was properly frozen to an external device.

11. The method of claim 1, further comprising sterilizing said biocontainer and said temperature sensor prior to receiving said biopharmaceutical material.

12. The method of claim 1, further comprising receiving electromagnetic waves, converting said electromagnetic waves to electrical power, and operating said temperature sensor, said processing unit, and said storage element with said electrical power.

* * * * *